(12) United States Patent
Heinecke

(10) Patent No.: US 6,268,220 B1
(45) Date of Patent: Jul. 31, 2001

(54) DIAGNOSTIC METHOD FOR ATHEROSCLEROSIS

(75) Inventor: Jay W. Heinecke, St. Louis, MO (US)

(73) Assignee: Washington University, St. Louis, MO (US)

( * ) Notice: Subject to any disclaimer, the term of this patent is extended or adjusted under 35 U.S.C. 154(b) by 496 days.

(21) Appl. No.: 08/709,916

(22) Filed: Sep. 9, 1996

(51) Int. Cl.$^7$ ................................................. G01N 33/566
(52) U.S. Cl. ..................... 436/501; 436/518; 436/811; 435/7.1; 435/7.92; 435/40.52; 435/69.6; 250/282
(58) Field of Search ........................... 73/61.52; 250/282; 435/7.1, 7.92, 40.52; 436/501, 518, 81, 69.6

(56) References Cited

PUBLICATIONS

Domigan et al., "Chlorination of Tyrosyl Residues in Peptides by Myeloperoxidase and Human Neutrophils," *The Journal of Biological Chemistry*, vol. 270, No. 28, pp. 16542–16548, Jul. 14, 1995.*

Hazen et al., "3–Chlorotyrosine, a Specific Marker of Myeloperoxidase–Catalyzed Halogenation, is Present in Human Atherosclerotic Aorta," *Circulation* (Supplement 1) vol. 94, No. 8, pp. 1–2, abstract 0009, Oct. 15, 1996.*

Hazen et al., "Reactive Aldehydes Generated by Myeloperoxidase are the Major Products of Phagocyte Activation at Plasma Concentrations of Free Amino Acids: A Novel Pathway for Oxidative Damage at Sites of Inflammation and Vascular Disease," *Circulation* (Supplement 1) vol. 94, No. 8, p. I–707, abstract 4135, Oct. 15, 1996.*

Hazen et al., "Human Neutrophils Employ Chlorine Gas as an Oxidant during Phagocytosis," *Journal of Clinical Investigation*, vol. 98, No. 6, pp. 1283–1289, Sep. 1996.*

Anthony J. Kettle, "Neutrophils convert tyrosyl residues in albumin to cholorotyrosine," *FEBS Letters*, vol. 379, pp. 103–106, (1996).*

Berliner and Heinecke, *Free Radical Biol. & Med.*, vol. 20, pp. 707–727 (1996).

Daugherty et al., *J. Clin. Invest.*, vol. 94, pp. 437–444 (1994).

Heinecke et al., *J. Biol. Chem.*, vol. 268, pp. 4069–4077 (1993).

Heinecke et al., *J. Clin. Invest.*, vol. 91, pp. 2866–2872 (1993).

Hazen et al., *J. Biol. Chem.*, vol. 271, pp. 1861–1867 (1996).

Heinecke et al., *Biochemistry*, vol. 33, pp. 10127–10136 (1994).

Savenkova et al., *J. Biol. Chem.*, vol. 269, pp. 20394–20400 (1994).

Hazen et al., *J. Clin. Invest.*, vol. 98, No. 6, pp. 1283–1289 (1996).

Hazen et al., *J. Biol. Chem.*, vol. 271, No. 38, pp. 23080–23088 (1996).

Heinecke et al., *J. Clin. Invest.* vol. 77, pp. 757–761 (1986).

Hazen et al., *J. Clin. Invest.*, vol. 99, No. 9, May 1, 1997, pp. 2075–2081.

* cited by examiner

Primary Examiner—Bao-Thuy L. Nguyen
(74) Attorney, Agent, or Firm—Scott J. Meyer

(57) ABSTRACT

A diagnostic method and screening test for atherosclerosis and analogous diseases involving activated phagocytes and/or inflammation is provided which comprises determining the presence of 3-chlorotyrosine in a test sample of a body fluid or tissue at a level which is elevated relative to the level in a normal patient.

3 Claims, 4 Drawing Sheets

LDL from Atherosclerotic Aortae Contains Massive Levels of
3-Chlorotyrosine, a Marker of Myeloperoxidase-Catalyzed Oxidation

DIAGNOSTIC METHOD FOR ATHEROSCLEROSIS

This invention was made in part with government support under grant number AG 12293 awarder by the National Institutes of Health. The government has certain rights in the invention.

BACKGROUND OF THE INVENTION

This invention relates to a novel diagnostic method. More particularly, the invention is directed to a diagnostic method and screening test for atherosclerosis and analogous diseases involving activated phagocytes and/or inflammation such as, for example, arthritis, inflammatory bowel disease, ischemia-reperfusion injury and the like inflammatory and vascular diseases.

A leading cause of death in the United States is heart disease. About one million persons in the U.S. die of heart disease annually. Heart disease is actually a wide variety of diseases. The principal cause of many of them is atherosclerosis.

Atherosclerosis is a common form of arteriosclerosis in which fatty deposits, referred to as plaques, build up within the intima (inner wall of the arteries). As a consequence of the resulting narrowing on the arteries that feed blood to the heart, the heart's supply of oxygen, which is carried by the blood, is reduced. When blood supply is diminished appreciably, the individual may feel the pain of angina pectoris. Such pain is frequently exacerbated when the heart requires an unusually large amount of blood, e.g., during emotional stress or exercise. When the hear is thus deprived of its oxygen supply, heart muscle tissue dies. That is, a coronary occlusion or myocardial infarction may result, which can be fatal if a large area of tissue is affected.

Therefore, when an individual experiences the symptoms of angina pain, prompt contact with medical help is advised. Quick medical attention may be necessary to prevent a myocardial infarction or to provide therapeutic intervention if it has already occurred.

Although there are numerous therapeutic agents which have been used for combating heart disease, their use may be limited in instances where excessive tissue damage has already occurred. Surgical intervention such as angioplasty or bypass surgery may be indicated.

In view of the foregoing, it is apparent that a diagnostic method and screening test for atherosclerosis would have significant practical use in the medical field. Such a diagnostic would be useful for instituting precautionary measures within the individual's control, such as diet, exercise, etc., or administering therapeutic intervention before the onset of a myocardial infarction.

Accordingly, it is a principal object of the present invention to provide a diagnostic method or preventive screening test for atherosclerosis and analogous diseases involving activated phagocytes and/or inflammation such as, for example, arthritis, inflammatory bowel disease, ischemia-reperfusion injury and the like inflammatory and vascular diseases.

It is a further object to provide a diagnostic method for atherosclerosis which preferably is essentially non-invasive to the patient, as distinguished from invasive procedures such as, for example, cardiac catheterization.

(Note: Literature references on the following background information and conventional test methods and laboratory procedures well-known to the person skilled in the art, and other such state-of-the-art techniques as used herein, are indicated in parentheses, and appended at the end of the specification.)

It is known that an increased level of low density lipoprotein (LDL) is a major risk factor for development of atherosclerotic vascular disease (1). Previous reports indicate that LDL must be oxidized to trigger the pathological events of atherosclerosis (2,3). However, the underlying pathways for oxidation in vivo have not heretofore been identified. A mechanism considered herein involves myeloperoxidase, a heme protein secreted by activated phagocytes (3,6).

Myeloperoxidase uses hydrogen peroxide ($H_2O_2$) generated by phagocytes to generate potent microbicidal and cytotoxic agents (7–9). Catalytically active myeloperoxidase is present in human atherosclerotic lesions, where it co-localizes with lipid-laden macrophages, the cellular hallmark of the early atherosclerotic lesion (10). Patterns of immunostaining for the enzyme at different stages of atherosclerosis are remarkably similar to those for protein-bound lipid oxidation products (11).

The best characterized product of myeloperoxidase is hypochlorous acid (HOCl; refs. 5,7):

$$Cl + H_2O_2 + H^+ = HOCl + H_2O \tag{Equation 1}$$

This potent oxidant chlorinates electron-rich substrates and oxidatively bleaches heme groups (9,12–15). LDL exposed to reagent HOCl at neutral pH becomes aggregated and is rapidly taken up and degraded by macrophages (16).

Lipoproteins with similar properties that are rich in apolipoprotein B100, the major protein of LDL, have been isolated from atherosclerotic lesions (6,17–19). The unregulated uptake of modified LDL may be of critical importance in converting macrophages into foam cells (1–3). A monoclonal antibody which reacts selectively with HOCl-modified proteins recognizes epitopes in human atheroma and in LDL-like particles isolated from atherosclerotic tissue (6).

Myeloperoxidase is the only human enzyme known to generate HOCl at physiological concentrations of halide (7,20). However, most oxidation products generated by HOCl are either non-specific or decompose to yield uninformative compounds (9,21,22). Recent in vitro studies demonstrate that the myeloperoxidase-$H_2O_2$—$Cl^-$ system oxidized L-tyrosine to yield 3-chlorotyrosine (23–25).

BRIEF DESCRIPTION OF THE INVENTION

In accordance with the present invention a diagnostic method and screening test for atherosclerosis and analogous diseases involving activated phagocytes and/or inflammation is provided.

The method comprises determining the presence of 3-chlorotyrosine as a highly selective and sensitive marker for myeloperoxidase-mediated oxidative damage in a body fluid or tissue.

Detection of 3-chlorotyrosine in the body fluid or tissue of a patient at a level which is substantially elevated relative to the level in a normal patient thereby is useful for screening for atherosclerosis and a wide variety of diseases involving activated phagocytes and/or inflammation.

The diagnostic method also is useful as an assay for oxidative stress in vivo and for monitoring the effectiveness of therapeutic intervention for atherosclerosis and analogous diseases involving activated phagocytes and/or inflammation.

The body fluid or tissue for use in the diagnostic method can be, e.g., blood serum or plasma, urine or body tissues or cells containing metabolic products of activated phagocytes.

In accordance with the invention, it was found that activated phagocytes employ myeloperoxidase to chlorinate the aromatic ring of tyrosine residues on apolipoprotein B100 of LDL. Analysis of human atherosclerotic lesions revealed a 10-fold increase in the content of protein-bound 3-chlorotyrosine in comparison with normal aortic intima. Moreover, the level of 3-chlorotyrosine was 100-fold higher in lesion LDL compared with circulating LDL. The detection of 3-chlorotyrosine in human atherosclerotic aorta and in LDL isolated from atherosclerotic lesions thus indicates that myeloperoxidase is an important pathway for the oxidative modification of lipoproteins, and therefore a pivotal agent in the development of vascular disease.

The detection of 3-chlorotyrosine in human atherosclerotic tissues as shown herein indicates that $Cl_2$ may serve as a reactive intermediate for LDL oxidation in vivo.

The results herein provide the first direct evidence that myeloperoxidase executes halogenation reactions in vivo. The links between lipoprotein oxidation and reactive intermediates generated by myeloperoxidase implicate the enzyme in LDL oxidation in vivo, and show that 3-chlorotyrosine represents a rational diagnostic marker for screening whereby specific interventions designed to prevent human atherosclerotic vascular disease can be utilized.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments taken in conjunction with the accompanying drawings in which, briefly:

Following a 60 min incubation, neutrophils were removed by centrifugation. The supernatant was delipidated and dialyzed, $^{13}$C-labeled internal standards were added, and the samples were then subjected to acid hydrolysis. The content of L-tyrosine and 3-chlorotyrosine in acid hydrolysates were determined by stable isotope dilution GC-MS analysis as described under "Method", below.

Additions or deletions to the complete system were as indicated. The final concentrations of additions were:

---
3-Aminotriazole (3-AT), 10 mM;
$NaN_3$, 1 mM;
NaCN, 1 mM;
Catalase (Cat), 10 $\mu$G/ML;
Superoxide dismutase (SOD), 10 $\mu$g/ml; and
Ionomycin (Iono), 1 $\mu$M.
---

3-Chlorotyrosine content of LDL is normalized to the content of the precursor amino acid L-tyrosine. Values are the mean of duplicate determinations. Similar results were observed in three independent experiments.

Figure 2:
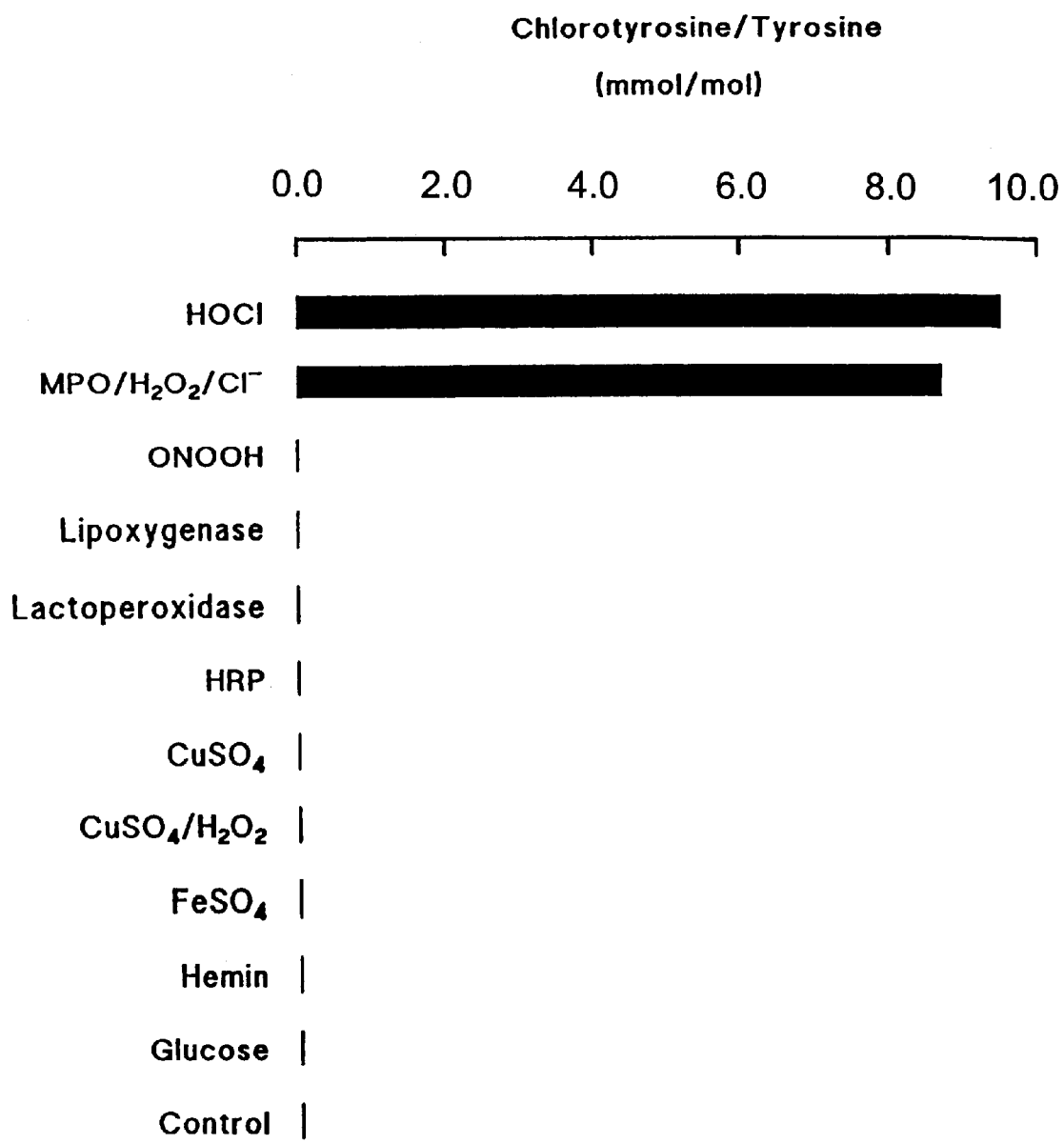

FIG. 2 show production of 3-chlorotyrosine in LDL modified by different oxidation systems. LDL (512 $\mu$g protein/ml) was incubated at 37° C. in phosphate buffered saline (10 mM sodium phosphate, 150 mM NaCl, pH 7.4) alone (Control) or with the indicated oxidation system. The complete myeloperoxidase-$H_2O_2$—$Cl^-$ system consisted of 20 nM myeloperoxidase and 100 $\mu$M $H_2O_2$. HOCl was used at 100 $\mu$M. Horseradish peroxidase (10 $\mu$g/ml and lactoperoxidase (10 $\mu$g/ml) were used with 100 $\mu$M $H_2O_2$. LDL was exposed to myeloperoxidase, HOCl, horseradish peroxidase and lactoperoxidase for 60 min.

All other oxidation reactions were carried out for 24 h. Final concentrations of oxidants were: peroxynitrite, 100 $\mu$M; $CuSO_4$, 10 $\mu$M; $CuSO_4$ and $H_2O_2$, 100 $\mu$M and 2 mM, respectively; $FeSO_4$, 10 $\mu$M; hemin, 10 $\mu$M; and glucose, 100 mM. LDL oxidation by lipoxygenase was performed in 50 mM borate, 150 mM NaCl supplemented with phospholipase $A_2$ as previously described (45).

Reaction products were delipidated, acid hydrolyzed, and the 3-chlorotyrosine content of the amino acid hydrolysate determined by stable isotope dilution GC-MS analysis. Values are the mean of duplicate determinations. Similar results were observed in three independent experiments. HRP, horseradish peroxidase; MPO, myeloperoxidase-peroxidase.

Figure 3:
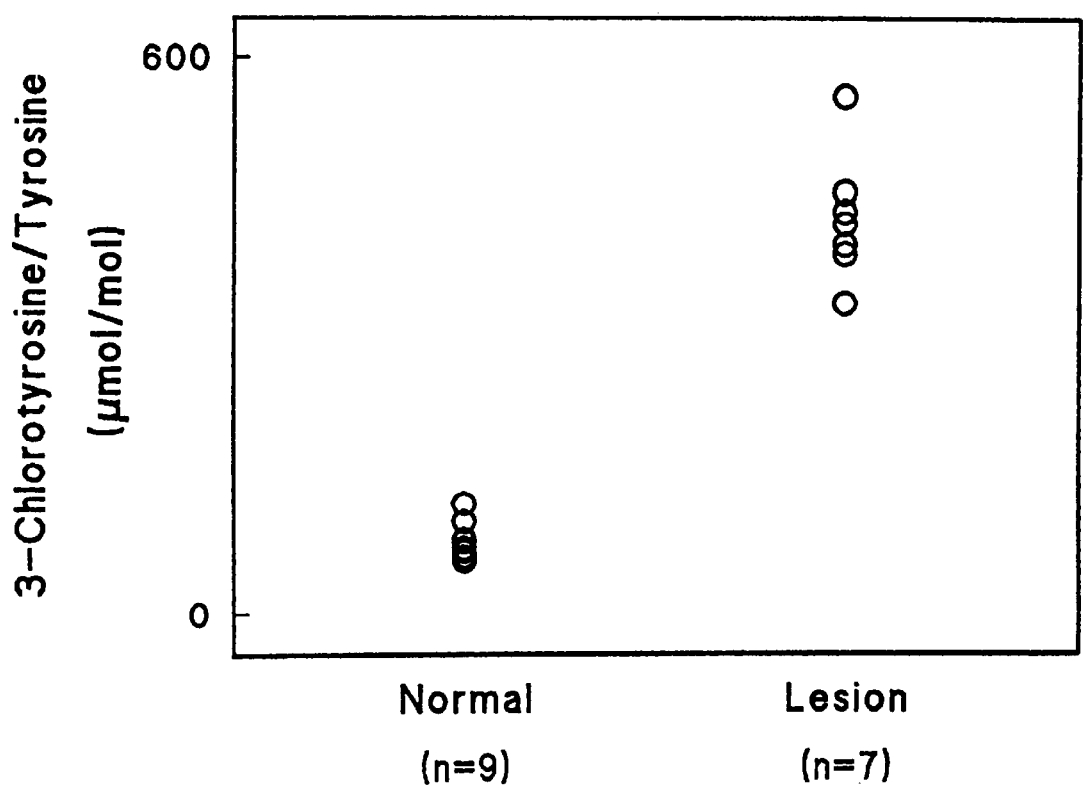

FIG. 3 shows 3-Chlorotyrosine content of normal and atherosclerotic human aortic tissue. Human thoracic aortic tissue obtained at surgery was immediately placed in ice-cold antioxidant buffer and frozen at −80° C. until analysis. Intima from normal and advanced atherosclerotic lesions was pulverized in liquid $N_2$, delipidated, dialyzed, spiked with $^{13}$C-labeled internal standards and subjected to acid hydrolysis. Amino acids in hydrolysates were then isolated by solid phase extraction on a C18 column, derivatized and subjected to stable isotope dilution GC-MS analysis as described under "Methods."

Figure 4:
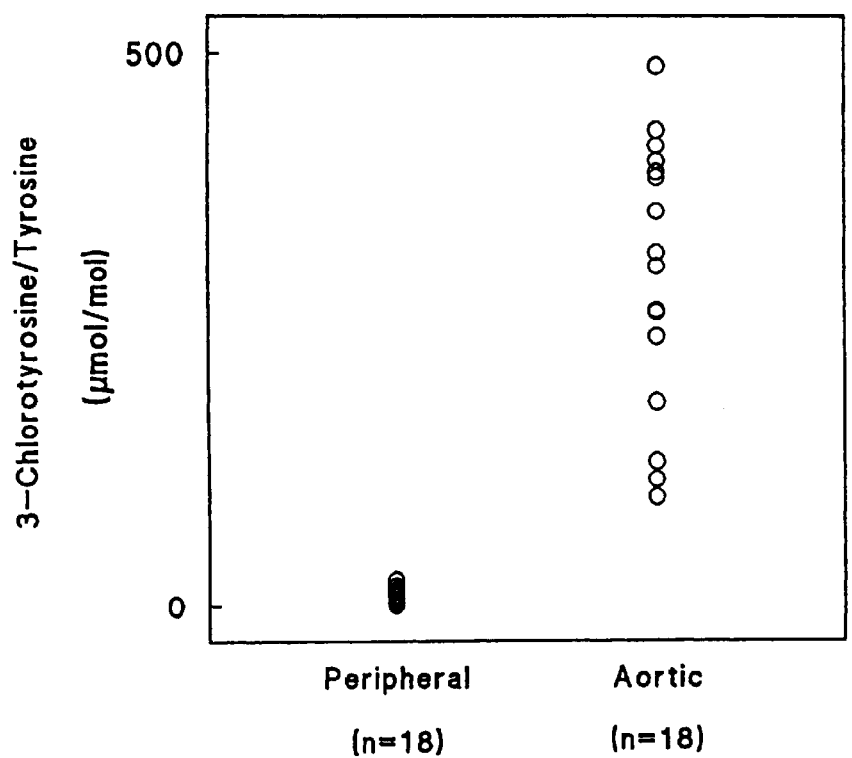

FIG. 4 shows level of 3-chlorotyrosine in LDL recovered from human atherosclerotic tissue and from plasma. LDL was isolated by sequential ultracentrifugation from plasma and atherosclerotic aorta, respectively, as described under "Methods". 3-chlorotyrosine content of the lipoproteins was determined by stable isotope dilution GC-MS analysis.

In order to further illustrate the invention in greater detail, the following Examples were carried out although it will be appreciated that the invention is not limited to these specific examples or the details described therein.

EXAMPLES

Materials

Peroxynitrite was a gift from Monsanto Corporation (St. Louis, Mo.). Rabbit anti-human apolipoprotein B100 antiserum was a gift from Dr. Gustav Schonfeld (Washington University, St. Louis, Mo.). All other reagents were purchased from either Sigma Chemical Co. or the indicated sources.

Methods

General Procedures—All glassware was rendered chlorine-demand free (<3% consumption of 1 mM HOCl in a 10 min incubation at 37° C. within a gas-tight vial as monitored by the oxidation of iodide to triiodide) prior to use (12,25,27). Buffers were treated with Chelex-100 resin to remove transition metal ions and demonstrated to be chlorine-demand free. Myeloperoxidase (donor: hydrogen peroxide, oxidoreductase, EC 1.11.1.7) was isolated (final $A_{430}/A_{280}$ ratio of 0.6) as previously described (28,29). Enzyme concentration was determined spectrophotometrically $\epsilon_{430}$=170 $mN^{-1}$ $cm^{-1}$; ref. 30). Human neutrophils were isolated by buoyant density centrifugation (31). Medium A (Hank's balanced salt solution (magnesium-, calcium-, phenol- and bicarbonate-free; Gibco-BRL, Gaithersburg, Md.), pH 7.2, supplemented with 100 µM diethylenetriamine pentaacetic acid (DTPA) was used for neutrophil isolation and experiments.

L-3-[$^{13}C_6$]chlorotyrosine was synthesized from L-[$^{13}C_6$] tyrosine using reagent HOCl and quantified by reverse phase HPLC analysis (25,26). Protein concentration was determined utilizing the Markwell-modified Lowrey protein assay (32) with bovine serum albumin (BSA) as standard. $H_2O_2$ concentration was determined spectrophotometrically ($\epsilon_{240}$=39.4 $M^{-1}cm^{-1}$; ref 33). LDL (d=1.019–1.070 g/ml) was isolated from non-fasted healthy male and female subjects by sequential density ultracentrifugation (34). SDS-PAGE was performed as described by Laemmli (35) with Western blot analysis using a rabbit anti-human apolipoprotein B100 antiserum and a control non-immune antiserum (36).

Tissue Collection—Fresh specimens of human aortic tissue were obtained from transplant donors and vascular surgery patients. Tissues were immediately rinsed in ice-cold normal saline, placed in Buffer A (65 mM sodium phosphate, pH 7.4, 100 µM DTPA, 100 µM butylated hydroxy toluene (BHT)), and frozen under $N_2$ at −80° C. until analysis. LDL was isolated from the intima of thoracic aortas obtained at necropsy within 10 h of death. Autopsy tissue was rinsed in ice-cold phosphate buffered saline supplemented with DTPA (100 µM) and immediately frozen in Buffer A under $N_2$ at −80° C. until analysis. Control studies demonstrated no detectable change in 3-chlorotyrosine content of tissues stored for up to 6 months under these conditions.

Tissue Processing—Surgical aortic specimens were thawed in sealed bags filled with Buffer A supplemented with 10 mM 3-aminotriazole, a myeloperoxidase inhibitor. All subsequent steps were performed at 4° C. unless otherwise indicated. Atherosclerotic lesions were classified morphologically using the criteria of the Pathobiological Determinants of Atherosclerosis in Youth Study (37). Aortic intima were resected from the media, frozen in liquid $N_2$, and pulverized under liquid $N_2$ with a stainless steel mortar and pestle.

Tissue powder (~20 mg wet weight) was suspended in 1 ml Buffer B ($H_2O$ supplemented with 100 µM DTPA and 10 mM 3-aminotriazole), and then delipidated three times at 0° C. The single-phase extraction mixture ($H_2O$:methanol:water-washed diethylether (1:3:7; v:v:v)) was vortexed, incubated for 30 min at 0° C., and the protein recovered by centrifugation (5000×g for 10 min at 0° C.). The protein powder was suspended in Buffer B, dialyzed against a buffer comprised of 50 mM Na[$PO_4$], pH 7.0, 100 µM DTPA and 10 mM 3-aminotriazole to remove chloride, and then dialyzed against Buffer B overnight.

LDL Isolation from Human Atherosclerotic Intima—LDL from vascular tissues was isolated by the method of Steinbrecker et al. (19) employing Buffer C (0.15 M NaCl, 10 mM sodium phosphate (pH 7.4), 1 mM EDTA, 100 µM DTPA, 50 µg/ml soybean trypsin inhibitor, 100 µM BHT, 1 µM phenylmethylsulfonylfluoride and 10 mM 3-aminotriazole) which contains antioxidants, protease and myelo-peroxidase inhibitors. Isolated thoracic aortae were thawed in sealed bags filled with Buffer C.

Fatty streaks and intermediate lesions were resected from media (~9 g wet weight per aorta), frozen in liquid $N_2$, pulverized under liquid $N_2$ with a stainless steel mortar and pestle, and intimal powder collected into 50 ml sterile conical tubes. Buffer C was added (5 ml per g wet weight tissue) and the tubes were rocked end-over-end overnight at 4° C. Samples were then spun at 5000×g for 15 min at 4° C., and the supernatant subjected to centrifugation at 100,000×g for 30 min at 4° C. The pellet and uppermost lipemic layer were discarded.

LDL-like particles in the remaining supernatant were isolated by sequential density ultracentrifugation (d =1.019–1.070 g/ml) (34). A metal chelator (100 µM DTPA) and myeloperoxidase inhibitor (10 mM 3-aminotriazole) were included in all solutions used for lipoprotein isolation.

Protein Hydrolysis—HBr was used for protein hydrolysis because preliminary experiments demonstrated that 3-chlorotyrosine was generated in L-tyrosine exposed to HCl. Following the addition of 10 pmol 3-[$^{13}C_6$] chlorotyrosine and 100 nmol L-[$^{13}C_6$]tyrosine, delipidated and dialyzed protein (~1–4 mg) suspended in Buffer B was dried under vacuum in a glass reaction vial. Each vial then received 0.5 ml HBr (6 N) containing 1% phenol.

The reaction vials were alternately degassed under vacuum and purged with argon five times, and incubated at 120° C. for 24 hours. Following hydrolysis, 1.5 ml of 0.1% trifluoroacetic acid (TFA) was added, and the mixture immediately passed over a solid phase C18 extraction column (Supelclean LC-18 SPE tubes, 3 ml; Supelco Inc., Bellefonte, Pa.) equilibrated with 0.1% TFA. The column was washed with 2 ml of the same buffer, eluted with 2 ml of 50% methanol in 0.1% TFA, and the recovered amino acids dried under vacuum.

Mass Spectrometric Analysis—n-Propyl, perheptafluorobutyl (HFB) and n-propyl, perpentafluoroproprionyl (PFP) derivatives of amino acids were prepared (38) and analyzed on a Hewlett Packard 5890 Gas Chromatograph interfaced with a Hewlett Packard 5988A Mass Spectrometer equipped with extended mass range. Chromatographic separations were typically carried out utilizing a 30 m DB-17 capillary column (Hewlett Packard; 0.2 mm i.d., 0.25 µm film thickness) in the splitless mode with He as the carrier gas. The column was run with the following temperature gradient: 150° C. to 250° C. at 20° C./ min with the injector, transfer line and source temperatures set at 250° C., 250° C. and 130° C., respectively.

Amino acids were quantified utilizing stable isotope dilution GC-MS analysis in the negative-ion chemical ionization mode (25,26). 3-Chlorotyrosine was monitored as its n-propyl-per-HFB derivative utilizing selected ion monitoring of the base peak at mass-to-charge ratio (m/z) 451 ($M^{-}$-HFB), another prominent ion at m/z 629 ($M^{-}$-HF), and their isotopically labeled internal standard ions at m/z 457 and 635, respectively.

L-Tyrosine was monitored as its n-propyl-per-HFB derivative using the base peak at m/z 417 ($M^{-}$-HFB), another major ion at m/z 595 ($M^{-}$-HF), and their labeled internal standard ions at m/z 423 and 601, respectively. The limit of detection (signal/noise >10) was <10 fmol for all amino acids.

Results

Figure 1:
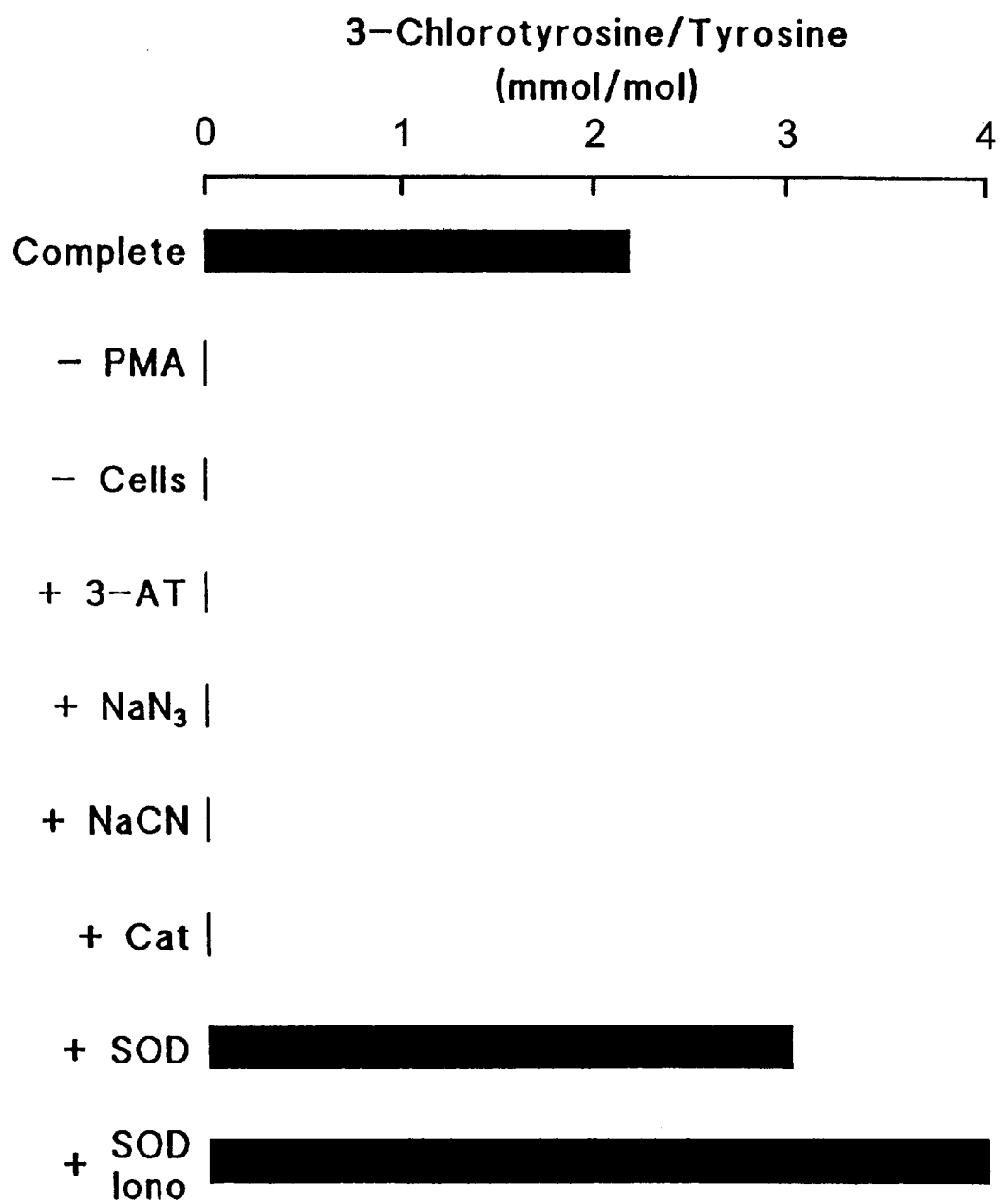
FIG. 1 shows formation of 3-chlorotyrosine in LDL exposed to activated human phagocytes. Human neutrophils ($1\times10^6$/ml) were incubated at 37° C. in Hank's Balanced Salt Solution supplemented with DTPA (100 $\mu$M) and LDL (512 $\mu$g protein/ml). Neutrophils were activated with phorbol ester (PMA; 200 nM) and maintained in suspensions by intermittent inversion (Complete neutrophil system).

3-Chlorotyrosine is a specific marker for LDL oxidation mediated by the myeloperoxidase-$H_2O_2$—$Cl^{31}$ system of activated phagocytes. To determine whether 3-chlorotyrosine formation serves as a marker for protein damage by myeloperoxidase, the levels of the oxidized amino acid in apolipoprotein B100 of LDL exposed to human neutrophils were quantified. No 3-chlorotyrosine could be detected by the mass spectrometric assay in freshly prepared LDL (detection limit <0.1 μmol per mol tyrosine). A dramatic increase in 3-chlorotyrosine content was apparent in LDL incubated with activated phagocytes (FIG. 1). Formation of 3-chlorotyrosine required activation of the cells with phorbol ester.

Addition of peroxidase inhibitors (azide, 3-aminotriazole and cyanide) and a peroxide scavenger (catalase) inhibited 3-chlorotyrosine production, implicating myeloperoxidase and $H_2O_2$ in the cell-mediated reaction.

Addition of superoxide dismutase (which catalyzes the conversion of $O_2^{·-}$ into $H_2O_2$) with and without the calcium ionophore ionomycin (which both enhances NADPH oxidase activation and stimulates myeloperoxidase secretion) resulted in further generation of the chlorinated amino acid. Collectively, these results implicate the myeloperoxidase-$H_2O_2$—Cl$^-$ system of phagocytes in the chlorination of tyrosyl residues of apolipoprotein B-100.

To investigate whether enzymatically generated HOCl was oxidizing LDL, the reaction requirements for chlorination of apolipoprotein B100 by myeloperoxidase (TABLE 1) were determined. The presence of the complete myeloperoxidase-$H_2O_2$—Cl— system resulted in 3-chlorotyrosine production. Chlorination required enzyme, $H_2O_2$ and Cl—, and was blocked by peroxidase inhibitors and catalase, implicating HOCl in the reaction pathway. Reagent HOCl resulted in 3-chlorotyrosine formation, confirming that HOCl generated by myeloperoxidase was an intermediate in the halogenation reaction.

To establish the specificity of 3-chlorotyrosine as a marker for protein damage by myeloperoxidase, the ability of a variety of in vitro oxidation systems to generate the chlorinated amino acid in apolipoprotein B100 of LDL was examined. Significant levels of 3-chlorotyrosine were detected in LDL exposed to the complete myeloperoxidase-$H_2O_2$—Cl$^-$ system and reagent HOCl (FIG. 2).

In contrast, there was little change in the 3-chlorotyrosine content of LDL oxidized by either copper, iron, a hydroxyl radical generating system ($H_2O_2$ plus copper), lactoperoxidase, horseradish peroxidase, peroxynitrite, glucose or lipoxygenase (FIG. 2). All of the systems resulted in LDL oxidation as monitored by the appearance of lipid oxidation products (thiobarbituric reacting substances assay and/or lipid hydroperoxides; refs. 27,34). Collectively, these results demonstrate that 3-chlorotyrosine production is a highly specific marker for LDL oxidation by the myeloperoxidase-$H_2O_2$—Cl$^-$ system.

3-Chlorotyrosine is present at increased levels in human atherosclerotic tissue. To determine whether 3-chlorotyrosine might be formed in vivo by myeloperoxidase, a search was made for the chlorinated amino acid in human atherosclerotic lesions. An inhibitor of myeloperoxidase was included in the buffers used for tissue processing to prevent ex vivo protein oxidation. Supplementation with myeloperoxidase failed to increase the levels of 3-chlorotyrosine in tissue subjected to the analytical procedure. These results indicate that generation of 3-chlorotyrosine by myeloperoxidase was unlikely to be taking place during tissue harvesting and processing.

When amino acids isolated from acid hydrolysates of atherosclerotic tissue were derivatized and analyzed by GC-MS, an amino acid was detected that exhibited major ions and a retention time identical to that of authentic 3-chlorotyrosine. The identity of the compound was confirmed by comparison with authentic standards using both heptafluorobutyryl and pentaflouropriopionyl derivatives of 3-chlorotyrosine. Selected ion monitoring demonstrated that the ions derived from the amino acid co-eluted with the ions derived from 3-[$^{13}C_6$]chlorotyrosine for both derivatives. These results indicate that protein-bound 3-chlorotyrosine is present in amino acid hydrolysates prepared from human atherosclerotic tissue.

To determine whether HOCl generated by myeloperoxidase might play a role in damaging proteins in atherosclerotic lesions, the levels of 3-chlorotyrosine in normal and atherosclerotic aortic tissue removed at surgery were quantified. Advanced atherosclerotic lesions exhibited a 10-fold increase in 3-chlorotyrosine content when compared with normal aortic tissue (FIG. 3)

Apolipoprotein B100 containing lipoproteins isolated from human atherosclerotic lesions demonstrate a marked increase in 3-chlorotyrosine. To assess directly the possible role of myeloperoxidase in catalyzing LDL oxidation in vivo, LDL (d=1.019–1.070 g/ml) was isolated from human atherosclerotic tissue recovered at autopsy, and then its 3-chlorotyrosine content was determined. A rabbit polyclonal antibody mono-specific for human apolipoprotein B100 detected a 500 kDa protein in lesion LDL, the predicted molecular mass of the protein. As previously noted by other investigators (6,17–19), a wide range of low molecular mass forms of immunoreactive protein were also present in LDL isolated from lesions.

Analysis of lesion LDL fractionated over a tandem set of Superose6 and Superose12 (Pharmacia-LKB Biotechnology, Piscattaway, N.J.) gel filtration columns demonstrated a major component which co-chromatographed with circulating LDL and which contained >95% of the immunoreactive apolipoprotein B100 protein (by ELISA).

Mass spectrometric analysis of LDL recovered from vascular lesions demonstrated levels of 3-chlorotyrosine that were 100-fold higher than those observed in circulating LDL (FIG. 4). These results indicate that one pathway for LDL oxidation in the human artery wall involves halogenation of the aromatic ring of L-tyrosine by myeloperoxidase.

TABLE I

The Myeloperoxidase-$H_2O_2$-Cl$^-$ System Oxidizes LDL to Yield 3-Chlorotyrosine.

| Condition | 3-Chlorotyrosine/L-Tyrosine (umol/mol) |
|---|---|
| Complete System | |
| LDL + MPO + $H_2O_2$ + Cl$^-$ | 50 |
| Complete System Minus | |
| MPO | 0 |
| $H_2O_2$ | 0 |
| Cl$^-$ | 0 |
| Complete System Plus | |
| Catalase (10 μg/ml) | 0 |
| NaN$_3$ (1 mM) | 0 |
| NaCN (1 mM) | 0 |
| 3-aminotriazole (10 mM) | 0 |
| LDL + HOCl (100 μM) | 68 |

The complete system consisted of Buffer B (20 mM Na[PO$_4$], pH 7.0, 100 μM DTPA) supplemented with LDL (512 μg protein/ml), myeloperoxidase (MPO; 40 nM), $H_2O_2$ (100 μM) and Cl$^-$ (as NaCl; 100 mM). After a 1 h incubation at 37° C., the 3-chlorotyrosine content was determined by stable isotope dilution GC-MS as described under "Methods." The limit of detection of the assay was <0.1 umol 3-chlorotyrosine per mol L-tyrosine. Values are the mean of duplicate determinations. Similar results were observed in three independent experiments.

Various other examples will be apparent to the person skilled in the art after reading the present disclosure without departing from the spirit and scope of the invention. It is intended that all such other examples be included within the scope of the appended claims. Thus, the presence and level of the 3-chlorotyrosine in the sample of body fluid or tissue also can be determined by immunoprecipitation procedures in an immunoassay with polyclonal or monoclonal antibodies to the 3-chlorotyrosine. One- and two-site radioimmunoassays and enzyme immunoassays, e.g., an enzyme-linked immunosorbent assay (ELISA) procedure as described by Engvall and Perlmann, *J. Immunol.* 109, 129–135 (1972), can be used in the diagnostic method of the invention.

Monoclonal antibodies for use in such procedures can be prepared by conventional hybridoma methodology as described by Köhler and Milstein, *Nature* 256, 495–497 (1975), and *Eur. J. Immunol.* 6, 511–519 (1976); and Goding, *Monoclonal Antibodies: Principles and Practice,* Academic Press Inc., New York (1983).

REFERENCES

1. Brown, M. S. and Goldstein, J. L. (1986) *Science* 232, 34–47
2. Witztum, J. L. and Steinberg, D. (1991) *J. Clin. Invest.* 88, 1785–1792
3. Berliner, J. A. and Heinecke, J. W. (1996) *Free Rad. Biol. & Med.* 20,707–727
4. Agner, K. (1972) in *Structure and Function of Oxidation-Reduction Enzymes* Akeson, A. and Ehrenberg, A., Eds.) pp. 329–335, Pergamon Press, New York
5. Klebanoff, S. J. and Clark, R. A. (1978) in *The Neutrophil: Function and Clinical Disorders* pp.447–451, Elsevier/ North Holland Biomedical Press, Amsterdam
6. Hazell, L. J., Arnold, L., Flowers, D., Waeg, D., Malle, E. and Stocker, R. (1996) *J. Clin. Invest* 97, 1535–1544
7. Harrison, J. E. and Schultz, J. (1976) *J. Biol. Chem.* 251, 1371–1374
8. Foote, C. S., Goyne, T. E. and Lehrer, R. I. (1981) *Nature* 301, 715–716
9. Albrich, J. M., McCarthy, C. A. and Hurst, J. K. (1981) *Proc. Natl. Acad. Sci. USA* 78, 210–214
10. Daugherty, A., Dunn, J. L. Rateri, D. L. and Heinecke, J. W. (1994) *J. Clin. Invest.* 94, 437–444
11. Rosenfeld, M. E., Palinski, W., Yla-Herttuala, S., Butler, S. and Witztum, J. L. (1990) *Arterio.* 10, 336–349
12. Weil, I. and Morris, J. C. (1949) *J. Amer. Chem. Soc.* 71, 1664–1671
13. Thomas, E. L., Jefferson, M. M. and Grisham, M. B. (1982) *Biochem.* 21, 6299–6308
14. Weiss, S. J., Klein, R., Slivka, A. and Wei, M. (1982). *J. Clin. Invest.* 70, 598–607
15. Heinecke, J. W., Li, W., Mueller, D. M., Boher, A. and Turk, J. (1994) *Biochem.* 33, 10127–10136
16. Hazell, L. J. and Stocker, R. (1994) *Biochem. J.* 290, 165–172
17. Dougherty, A., Zweifel, B. S., Sobel, B. E. and Schonfeld, G. (1988) *Arterio.* 8, 768–777
18. Yla-Hertulla, S., Palinski, W., Rosenfeld, M. E., Parthasarathy, S., Carew, T. E., Butler, S., Witztum, J. L. and Steinberg, D. (1989) *J. Clin. Invest.* 84, 1086–1095
19. Steinbrecher, U. D. and Lougheed, M. (1992) *Arteriosis and Thrombosis* 12, 608–625
20. Weiss, S. J., Test, S. T., Eckmann, C. M., Ross, D. and Regiani, S. (1986) *Science* 234, 200–203
21. Stetmaszynska, T. and Zygliczynski, J. M. (1978) *Eur. J. Biochem.* 92, 301–308
22. Zygliczynski, J. M., Stetmaszynska, T., Domanski, J. and Ostrowski, W. (1971) *Biochim. Biophys. Acta* 235, 419–424
23. Domigan, N. M., Charlton, T. S., Duncan, M. W., Winterbourn, C. C. and Kettle, A. J. (1995) *J. Biol. Chem.* 270, 16542–16548
24. Kettle, A. J. (1995) *FEBS Lett.* 379, 103–106
25. Hazen, S. L., Hsu, F. F., Mueller, D. M., Crowley, J. R. and Heinecke, J. W., (1996) *J. Clin. Invest.* (In Press)
26. Hazen, S. L., Crowley, J. R., Mueller, D. M. and Heinecke, J. W., "Mass Spectrometric Quantification of 3-Chlorotyrosine Content in Human Tissues with Atomol Sensitivity: a Marker Specific for Myeloperoxidase-Catalyzed Oxidation at Sites of Inflammation," (submitted).
27. El-Saadani, M., Esterbauer, H., El-Sayad, M., Goher, A., Nassar, A. Y. and Jurgens, G., (1989) *J. Lipid Res.* 30, 627–630
28. Heinecke, J. W., Li, W., Francis, G. A. and. Goldstein, J. A. (1993) *J. Clin. Invest.* 91, 2866–2872
29. Rakita, R. M., Michel, B. R. and Rosen, H. (1990). *Biochem.* 29, 1075–1080
30. Morita, Y., Iwamoto, H., Aibara, S., Kobayashi, T. and Hasegawa, E. (1986) *J. Biochem.* 99, 761–770
31. Hazen, S. L., Hsu, F. F. and Heinecke, J. W. (1996) *J. Biol. Chem.* 271, 1861–1867
32. Markwell, M. A., Haas, S. M., Bieber, L. L. and Tolbert, N. E. (1978) *Anal. Biochem.* 87, 206–210
33. Nelson, D. P. and Kiesow, L. A. (1972) *Anal. Biochem.* 49, 474–478.
34. Heinecke, J. W., Baker, L., Rosen, H. and Chait, A. (1986) *J. Clin. Invest.* 77, 757–761
35. Laemmli, U. K. (1970) *Nature* 227, 680–685
36. Krull, E. S., Tang, J., Ketter, T. S., Clouse, R. E., Schonfeld G. (1992) *Biochem. Biophys. Res. Com.* 189, 1069–1076.
37. PDAY Research Group (1993) *Arterio. Thromb.* 13, 1291–1298
38. Knapp, D. R. (1979) *Handbook of Analytical Derivitization Reactions,* John Wiley & Sons, New York
39. Hazell, L. J., van den Berg, J. J. M. and Stocker, R. (1994) *Biochem. J.* 302, 297–304
40. Hazen, S. L., Hsu, F. F., Duffin, K. and Heinecke, J. W. (1996) *J. Biol. Chem.* (In Press)
41. Morel, D. W. and DiCorleto, P. E. (1994) *Proc. Natl. Acad. Sci. USA* 91, 11452–11456
42. Kandutsch, A. A., Chen, H. W. and Heiniger, H. (1978) *Science* 201, 498–501
43. Sevanian, A. and Peterson, A. R. (1986) *Fd. Chem. Toxic.* 24, 1103–1110
44. Smith, L. L. and Johnson, B. H. (1989) *Free Rad. Biol. Med.* 7, 285–332

What is claimed is:

1. A diagnostic method and screening test for atherosclerosis comprising determining the presence of 3-chlorotyrosine in a test sample of a body tissue at a level which is elevated from about 10-fold to about 100-fold greater than the level in a normal subject.
2. The method of claim 1 in which the presence and level of 3-chlorotyrosine is determined by gas chromatography and mass spectrometric analysis.
3. The method of claim 1 in which the presence and level of 3-chlorotyrosine is determined by an immunoassay with antibodies to said 3-chlorotyrosine.

* * * * *